(12) United States Patent
Lemann

(10) Patent No.: US 6,333,026 B1
(45) Date of Patent: Dec. 25, 2001

(54) USE OF AN INDIGOID COMPOUND IN A COSMETIC COMPOSITION, IN PARTICULAR A MAKE-UP COMPOSITION, IN ORDER TO CONFER ON IT ANTIMICROBIAL PROPERTIES AND THE PROPERTY OF LENGTHY HOLD OVER TIME

(75) Inventor: Patricia Lemann, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/458,207

(22) Filed: Dec. 10, 1999

(30) Foreign Application Priority Data

Dec. 11, 1998 (FR) .................................................. 98 15693

(51) Int. Cl.[7] .................................................. A61K 7/021
(52) U.S. Cl. .............................. 424/63; 424/401; 424/59; 424/61; 424/64; 424/70.1
(58) Field of Search .............................. 424/401, 59, 61, 424/64, 70.1, 63

(56) References Cited

FOREIGN PATENT DOCUMENTS 2 771 286    5/1999   (FR) .

*Primary Examiner*—Jose' G. Dees
*Assistant Examiner*—Konata M. George
(74) *Attorney, Agent, or Firm*—Nixon & Vanderhye P.C.

(57) ABSTRACT

The invention relates to the use of at least one compound of formula:

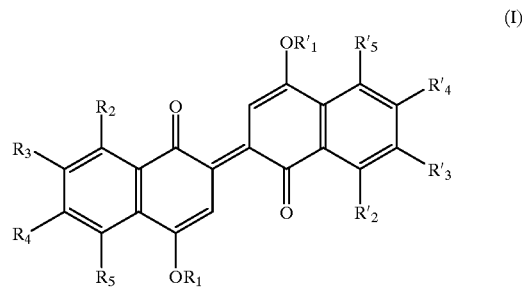

(I)

in which $R_1$ and $R'_1$ are $C_1$–$C_{18}$ alkyl radicals which are optionally substituted by one or more halogens or hydroxyls and/or are interrupted by one or more heteroatoms, and $R_2$ to $R_5$ and $R'_2$ to $R'_5$ are hydrogen or halogen atoms, hydroxyl radicals or $C_1$–$C_6$ alkyl, alkyloxy, acyl or acyloxy radicals, in a cosmetic composition, in particular a make-up composition, in order to confer on it antimicrobial properties and properties of lengthy hold over time and/or of non-migration and/or of freedom from transfer and/or of non-formation of streaks.

The invention also relates to a cosmetic composition, in particular a make-up composition and especially an eye-shadow, comprising such a compound in a silicone binder.

37 Claims, No Drawings

USE OF AN INDIGOID COMPOUND IN A COSMETIC COMPOSITION, IN PARTICULAR A MAKE-UP COMPOSITION, IN ORDER TO CONFER ON IT ANTIMICROBIAL PROPERTIES AND THE PROPERTY OF LENGTHY HOLD OVER TIME

A subject-matter of the present invention is the use of an indigoid compound in a cosmetic composition, in particular a make-up composition, in order to confer on it antimicrobial properties and the property of lengthy hold over time and/or the property of non-migration and/or the property of freedom from transfer and/or the property of non-formation of streaks, as well as a cosmetic composition, in particular a make-up composition, comprising such an indigoid compound in combination with a silicone binder.

Cosmetic compositions and in particular make-up compositions, such as free or compact powders, foundations, face powders, eyeshadows, lipsticks or nail varnishes, are composed of an appropriate vehicle and of various colouring agents intended to confer a certain colour on the said compositions before and/or after their application to the skin, mucous membranes, such as the internal part of the lower eyelids, semi-mucous membranes, such as the lips, and/or superficial body growths, such as the nails, eyelashes, eyebrows or hair.

A fairly limited range of colouring agents is used today to create colours, among which colouring agents may be mentioned compounds which are generally insoluble in aqueous and organic media, such as organic lakes, inorganic pigments or pearlescent pigments.

The pigments and lakes used in the make-up field are highly varied in origin and in chemical nature. Their physicochemical properties, in particular particle size, specific surface, relative density and the like, are therefore very different. These difference are reflected by variations in behaviour: their ease of use or dispersion in the medium, their stability with regard to light or to temperature, their mechanical properties, their hold over time, their colouring power and their covering power.

Thus, inorganic pigments, in particular inorganic oxides, such as iron oxides, ultramarine blue, Prussian blue (ferric ferrocyanide), cobalt blue ($CoOAl_2O_3$) or manganese violet, are very stable with regard to light and pH but give rather lifeless, dull and pale colours and/or colours with a weak colouring power, the colours being easily diluted when they are mixed with a white pigment of the titanium dioxide type, and/or colours with a weak covering power, that is to say transparent on application. It is therefore necessary to introduce a large amount of them into the cosmetic formulations in order to obtain a sufficiently saturated feature. This high percentage of inorganic particles can, nevertheless, affect the gloss of the composition, its homogeneity on application, its hold and its comfort. In addition, for manganese violet, the appearance of mould is observed at the surface of some compositions.

Use may also be made, in order to obtain coloured effects, of pearlescent pigments of varied but never very intense colours, which make it possible to obtain iridescent but mostly fairly weak effects.

In the field of temporary or transient hair colouring, which gives rise to a slight modification of the natural colour of the hair which lasts from one shampooing to another and which serves to beautify or correct a shade which has already been obtained, provision has already been made for colouring with conventional inorganic pigments, in order to introduce a temporary highlight to the hair, but the shades obtained by this colouring remain fairly lifeless, too uniform and not very playful.

In the field of make-up, only organic lakes have until now made it possible to obtain vivid or intense colours. However, most organic lakes exhibit very poor hold with regard to light, which results in a very marked attenuation in their colour over time, are very transparent on application, that is to say have little covering power, and have a weak colouring power. They can also be unstable with regard to temperature and/or pH. Furthermore, some lakes result in an excessive degree of bleeding, that is to say that they exhibit the disadvantage of staining the support to which they are applied. Thus, this can have the consequence of staining ocular lenses, in the case of eyeliners or mascaras, or of leaving a colouring on the skin or nails after the removal of make-up, in the case of lipsticks or nail varnishes. Finally, the instability of lakes is further exacerbated when they are used in combination with photoreactive pigments, such as titanium dioxide. In point of fact, these pigments are very widely used in make-up, in particular for protection against UV radiation. Consequently, the use of organic lakes in cosmetics is fairly limited, the consequence of which is a limitation in the tints achievable.

Thus, the need remains to have available colouring agents which can be used in cosmetics and which make it possible to obtain an appropriate colouring of the compositions and of the make-up film obtained, it being necessary for the said colouring agents not to migrate or to bleed onto the support on which the said compositions are deposited or not to transfer onto another support and it being necessary for the said colouring agents to have a high colouring power, a high covering power and a lengthy hold over time, without the appearance of streaks, in particular on the eyelids. Furthermore, these colouring agents must not promote the growth of mould.

After much research, the Applicant Company has demonstrated that the use of a very specific family of organic compounds makes it possible to obtain such a result.

Thus, a subject-matter of the invention is the use of at least one indigoid compound of formula (I):

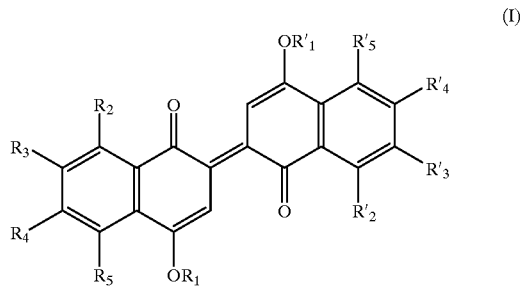

in which:
  $R_1$ and $R'_1$ are, independently of another, saturated or unsaturated, linear, branched or cyclic alkyl radicals having 1 to 18 carbon atoms which are optionally substituted by one or more halogens and/or by one or more hydroxyl radicals and/or interrupted by one or more heteroatoms;
  $R_2$, $R'_2$, $R_3$, $R'_3$, $R_4$, $R'_4$, $R_5$ and $R'_5$ are, independently of one another, chosen from a hydrogen atom, a halogen atom, a hydroxyl radical or a saturated or unsaturated, linear or branched, alkyl, alkyloxy, acyl or acyloxy radical having 1 to 6 carbon atoms, in a cosmetic composition, in particular a make-up composition, in order to confer on it at least one of decreasing or eliminating the migration potential of the cosmetic composition, decreasing or eliminating the transferability of the cosmetic composition, and decreasing or eliminating the streak forming capacity of a cosmetic composition, to impart, for example, properties of lengthy hold over time and/or of non-migration and/or of freedom from transfer and/or of non-formation of streaks, in particular on the eyelids.

Another subject-matter of the invention is the use of at least one indigoid compound of above formula (I) in the antimicrobial protection of cosmetic compositions, in particular make-up compositions.

It is usual to introduce silicone binders into cosmetic compositions, in particular make-up compositions, in order to facilitate the application and the spreading thereof while providing comfort and softness.

However, the inventor has found that the absence of non-volatile silicone oil in the silicone binder of make-up compositions has a tendency to decrease the hold over time of these compositions, in particular of eyeshadows. In the absence of non-volatile silicone oil, the eyeshadow is converted to powder and does not hold.

The inventor has discovered, surprisingly, that, by combining silicone oils, in particular non-volatile silicone oils, in cosmetic compositions, in particular make-up compositions, with an indigoid colouring agent of above formula (I), she obtains cosmetic compositions having not only good spreading, comfort and softness properties but also good properties of hold over time, both as regards the colour and the make-up.

Furthermore, the make-up compositions thus obtained can confer an intense, in particular blue, very saturated and very covering colour which does not fade over time. They do not migrate and do not bleed onto (do not stain) the support on which they are deposited; they do not transfer to another support and do not form streaks, in particular on the eyelids.

The inventor has also discovered, surprisingly, that the use of volatile silicone oils in the silicone binder of make-up compositions comprising an indigoid colorant of formula (I) confers advantageous transfer-free properties on the latter, that is to say properties of non-migration onto certain supports with which it can enter into contact, such as an item of clothing, a solid object or the skin.

Another subject-matter of the present invention is therefore a cosmetic composition, in particular a make-up composition, comprising, in a cosmetically acceptable medium comprising at least one non-volatile silicone oil, at least one indigoid compound of formula (I) as defined above.

The compounds used in the cosmetic composition of the invention are, in some cases, compounds known in the literature. Some have been disclosed in particular in the publication "2,2'-Binaphthyliden-1,1'-dione, Farbe and Struktur" [2,2'-Binaphthylidene-1,1'-dione, Colour and Structure] by Göltner et al., Liebigs Ann. Chem., 1991, pages 1085-1089. This publication discloses in particular a preparation process which makes it possible to obtain some of these compounds in the form of crystals with a mauve colour or blue colour ranging from pale blue to dark blue.

However, there is nothing in this publication which allows it to be envisaged that these compounds can be employed with success in cosmetic compositions, that is to say that they make possible the preparation of a cosmetically acceptable composition, capable of being applied to the skin, giving an intense, very saturated and very covering colour, having a lengthy hold over time, not migrating and not bleeding onto the support on which it is deposited, not transferring onto another support and not forming streaks, in particular on the eyelids.

The inventor has also found that, in addition, it is possible to adjust the colour of the compounds of formula (I) by varying the nature and/or the position of the various R substituents present on the molecule.

It is thus possible to obtain compounds with a colour which can vary from mauve to red, passing through blue and green.

Furthermore, the compounds used in the cosmetic composition of the invention exhibit good stability with regard to temperature, pH and light.

They are also readily accessible by chemical synthesis, even on an industrial scale.

In the above formula (I), the heteroatoms can be oxygen, silicon, nitrogen or sulphur atoms or groups of these atoms.

$R_1$ and/or $R'_1$ are preferably alkyl radicals having 1 to 8 carbon atoms and in particular methyl, ethyl, propyl, butyl, pentyl or hexyl radicals.

$R_2$ to $R_5$ and $R'_2$ to $R'_5$ preferably represent a hydrogen atom.

In particular, mention may be made, as compounds capable of being used according to the invention, of the following compounds:

4,4'-dimethyloxy-[2,2'-binaphthylidene]-1,1'-dione,
4,4'-diethyloxy-[2,2'-binaphthylidene]-1,1'-dione,
4,4'-diisopropyloxy-[2,2'-binaphthylidene]-1,1'-dione, and
4,4'-di(n-hexyloxy)-[2,2'-binaphthylidene]-1,1'-dione.

4,4'-Dimethyloxy-[2,2'-binaphthylidene]-1,1'-dione is preferred for use according to the invention as it makes it possible to obtain an intense blue colour with lengthy hold over time.

The compounds of formula (I) are provided in solid form. They produce vivid and varied colours, according to the nature of the substituents.

They are generally insoluble in water and have very little solubility in oils of varied nature and/or polarity. These compounds consequently exhibit the advantage of showing very little migration when they are used in compositions comprising fatty substances.

The compounds according to the invention can be easily prepared by a person skilled in the art on the basis of the prior art and of his general technical knowledge.

The compounds of formula (I) can be incorporated in a cosmetic composition, in particular a make-up composition, in an amount which can be between 0.5 and 30% by weight with respect to the total weight of the composition, preferably in an amount from 0.5 to 10% by weight.

The said compounds can be present in the composition in the free form or in the form of a combination with substrate particles, which they coat.

This is because it has been found that the compounds of formula (I) exhibit the distinguishing feature of being able to coat, at least partially, indeed even completely, substrate particles such as conventional pigments or fillers.

Mention may in particular be made, among particles capable of being coated by the compounds of formula (I), of metal oxide pigments or nanopigments, such as titanium, zinc, iron, manganese, cerium and/or zirconium oxides, fillers, such as talc, mica, silica, kaolin, or nylon and polyethylene powders, or microspheres, such as hollow microspheres formed of vinylidene chloride/acrylonitrile copolymers.

Talc is preferably chosen as substrate particle to be coated.

The pulverulent materials thus obtained, composed of the coated substrate particles, can then themselves be used as colouring agent in cosmetic compositions.

It has been found that the said pulverulent materials exhibit, under electron microscopy, a very homogeneous structure.

It has also been found that the said pulverulent materials can exhibit the properties and advantages of each of the starting materials; in particular, when talc, known to contribute softness, is coated, a coated talc is obtained which retains its softness.

Furthermore, the use of a very small amount of compound of formula (I) coating a conventional filler makes it possible to obtain a colouring agent which has a high colouring strength, even used in a small amount, and which contributes appropriate coverage, as well as a colour having good hold with regard to light.

Use will preferably be made of the compounds of formula (I) in an amount of 0.1 to 100 parts by weight per 100 parts by weight of substrate particles to be coated.

The coated pulverulent material is preferably composed of 1 to 20% by weight of compounds of formula (I) and of 80 to 99% by weight of substrate particles. However, it is possible to envisage a coated pulverulent material composed of 50% by weight of compounds of formula (I) and of 50% by weight of substrate particles.

The pulverulent material, composed of substrate particles which are at least partially coated with the compound of formula (I), will generally be prepared in the following way:

in a first step, the compound of formula (I) is dissolved in an appropriate solvent, for example dimethylformamide, then the said compound is precipitate on the substrate particle to be coated, for example by adding the solution of the said compound to an aqueous dispersion or suspension of the said particle.

The pulverluent material can subsequently be filtered off, washed and dried according to conventional techniques.

The said compounds of formula (I) and/or the said pulverulent materials can be used in particular as colouring agents in a cosmetic composition which can be provided in the form of a product to be applied to the lips and/or keratinous materials, such as the skin and superficial body growths (nails, eyelashes, eyebrows and hair, including body hair).

The said composition therefore comprises a cosmetically acceptable medium, that is to say a medium compatible with all keratinous substances, such as the skin, nails, hair, eyelashes and eyebrows, lips and any other cutaneous region of the body and face.

The said medium can comprise or be provided in the form of, in particular, a suspension, a dispersion or a solution in solvent or aqueous/alcoholic medium which is optionally thickened, indeed even gelled; an oil-in-water, water-in-oil or multiple emulsion; a gel or a foam; an emulsified gel; a dispersion of vesicles, in particular lipid vesicles; a two-phase or multiphase lotion; a spray; a free, compact or cast powder; or an anhydrous paste.

A person skilled in the art can choose the appropriate pharmaceutical dosage form, as well as its method of preparation, on the basis of his overall knowledge, taking into account, on the one hand, the nature of the constituents used, in particular their solubility in the vehicle, and, on the other hand, the application envisaged for the composition.

The cosmetic composition according to the invention comprises a fatty phase comprising at least one non-volatile silicone oil and optionally a volatile silicone oil.

The term "silicone oil" means any fluid silicone and in particular any silicone which is liquid at room temperature and atmospheric pressure, as well as any silicone solution.

The silicone oils can be silicone surfactants or can comprise silicone surfactants, such as alkyl, alkoxy or aryl dimethicone copolyols in which the alkyl, alkoxy or aryl chain comprises 1 to 24 carbon atoms and can be a pheny radical and in particular a cetyl radical.

Mention may also be made, as examples of silicone oils used in the invention, of:

non-volatile polyalkylsiloxanes with a $C_1$–$C_{24}$ alkyl chain and with trimethylsilyl end groups, preferably those with a viscosity at 25° C. of less than or equal to 0.06 $m^2/s$, among which may be mentioned linear polydimethylsiloxanes, such as dimethicones (CTFA name) and in particular those sold under the name "Dow Corning Fluid 200" by the Company Dow Corning, alkylmethylpolysiloxanes, such as cetyl dimethicone (CTFA name), and the products sold under the names "AK" by the company Wacker, "SF" by the company General Electric and "Abil" by the company Goldschmidt, such as the product "Abil 10";

non-volatile silicones modified by optionally fluorinated aliphatic and/or aromatic groups or by hydroxyl, thiol and/or amine groups;

phenylated non-volatile silicone oils, such as phenyl trimethicones and phenyl dimethicones; mention may in particular be made of those disclosed in EP-A-665,008 and more particularly the products sold under the names "Abil AV 8853" by the Company Goldschmidt, "DC 556" and "SF 558" by the Company Dow Corning, "Silbione 70633 V30" by the Company Rhône-Poulenc and "Belsil PDM 100", "Belsil PDM 200" or "Belsil PDM 1000" by the Company Wacker;

cyclic silicones which are volatile at room temperature (25° C.) having from 3 to 8 silicon atoms and preferably 4 to 6, such as, for example, cyclomethicones, such as cyclotetradimethylsiloxane, cyclopentadimethylsiloxane (D5) or cyclohexadimethylsiloxane (D6), and the products sold under the names "DC Fluid 244", "DC Fluid 245", "DC Fluid 344" and "DC Fluid 345" by the company Dow Corning, as well as those sold under the names "Abil K4" by the company Goldschmidt, under the names "Silbione 70045 V2" and "Silbione Oil 70045 V5" by the company Rhône-Poulenc, and under the names "Volatile Silicone 7158" and "Volatile Silicone 7207" by the company Union Carbide;

non-volatile cyclocopolymers of the dimethylsiloxane/methylalkylsiloxane type, such as "Silicone FZ 3109", sold by the Company Union Carbide, which is a dimethylsiloxane/methyloctylsiloxane cyclocopolymer;

linear volatile silicones having from 2 to 9 silicon atoms, optionally comprising a pendant $C_2$–$C_{10}$ alkyl chain or a $C_2$–$C_{10}$ alkyl chain at the chain end, for example hexamethyldisiloxane, hexylheptamethyltrisiloxane and octaheptamethyltrisiloxane; and their mixtures.

The non-volatile silicone oils can also be liquid resins, such as isostearyl trimethylolpropane siloxysilicates.

The silicone oils used according to the invention are preferably present in a proportion of at least 0.5% and preferably of at least 4% by weight with respect to the total weight of the composition. In the case of an eyeshadow, the amount of silicone oil can range up to 70% of the total weight of the composition and can represent in particular from 4 to 40% by weight of the total weight of the composition.

The composition according to the invention can also comprise other silicone compounds, such as silicone gums and silicone waxes.

The silicone gums which can be used in the composition of the invention can be polysiloxanes with a high molecular mass, of the order of 200,000 to 1,000,000, and with a viscosity of greater than 500,000 mPa·s. They can be used alone or as a mixture with a solvent, such as a polydimethylsiloxane or polyphenylsiloxane oil or a cyclomethicone.

The silicone waxes which can be used in the composition according to the invention can be substituted linear polysiloxanes. Mention may be made, for example, of polyether silicone waxes, or alkyl or alkoxy dimethicones having from 16 to 45 carbon atoms.

The compositions according to the invention can also comprise non-silicone fatty substances, including pasty fatty substances, gums, waxes and oils of vegetable, mineral, animal or synthetic origin.

The term "wax" means a compound which is solid at room temperature, which is generally crystalline and which has a melting point of greater than 45° C.

Pasty fatty compounds can be defined using at least one of the following physicochemical properties:
a viscosity of 0.1 to 40 Pa·s (1 to 400 poises), measured at 40° C. with a Contraves TV rotary viscometer equipped with an MS-r3 or MS-r4 rotor at a frequency of 60 Hz,
a melting point of 25–70° C., preferably 25–55° C.

Mention may be made, as waxes which can be used in the invention, of waxes of animal origin, such as lanolin, beeswax, spermaceti or lanolin derivatives, such as lanolin alcohols, hydrogenated, hydroxylated or acetylated lanolin, lanolin fatty acids and acetylated lanolin alcohol; waxes of vegetable origin, such as carnauba, candelilla, kapok, ouricury, rice, hydrogenated jojoba, alfa or japan wax or cork fibre or sugar cane waxes or alternatively cocoa butter; mineral waxes, for example paraffin, montan, lignite, petrolatum or petroleum waxes or microcrystalline waxes, ceresin or ozokerite; or synthetic waxes, such as polyethylene waxes, the waxes obtained by the Fischer-Tropsch synthesis and the linear esters resulting from the reaction of a saturated $C_{10}$ to $C_{40}$ carboxylic acid and of a saturated $C_{10}$ to $C_{40}$ alcohol, such as myristyl myristate. Use may also be made of calcium lanolates or stearates and hydrogenated jojoba or coconut oil.

The fatty phase can also comprise one or more hydrocarbonaceous or fluorinated oils (s).

Mention will be made as hydrocarbonaceous oil, of: any fluid oil (or mixture of oils) which is stable at the usual temperature of use of cosmetic, pharmaceutical or hygiene products, such as oils of vegetable or animal, mineral or synthetic origin, or triglycerides of $C_{12}$ to $C_{18}$ fatty acids.

Mention may be made, among modified or unmodified oils of vegetable or animal origin, of, for example, sweet almond oil, avocado oil, castor oil, olive oil, jojoba oil, sunflower oil, wheat germ oil, sesame oil, groundnut oil, grape seed oil, soybean oil, rapeseed oil, safflower oil, coconut oil, maize oil, hazelnut oil, karite butter, palm oil, apricot kernel oil, calophyllum oil or perhydrosqualene.

Mention may be made, among oils of mineral origin, of, for example, liquid paraffin and liquid petrolatum.

Mention may in particular be made, among synthetic oils, of fatty acid esters, such as isopropyl myristate, isopropyl palmitate, 2-ethylhexyl palmitate, purcellin oil (stearyl octanoate), isononyl or isostearyl isononanoate or isopropyl lanolate, fatty acids, such as oleic, palmitic, stearic, behenic, linoleic and linolenic acids, or volatile or non-volatile isoparaffins, such as $C_8$–$C_{16}$ isoparaffins and polyisobutenes.

When the composition is provided in the aqueous form, in particular in the form of a dispersion or emulsion, it can comprise an aqueous phase, which can comprise water, a floral water and/or a mineral water.

The said aqueous phase can comprise from 0.5 to 20% by weight, with respect to the total weight of the aqueous phase, of a lower $C_2$–$C_6$ monoalcohol and/or of a polyol, such as glycerol, butylene glycol, isoprene glycol, propylene glycol or polyethylene glycol.

When the composition according to the invention is provided in the form of an emulsion, it can, in addition, optionally comprise a surfactant, preferably in an amount of 0.01 to 30% by weight with respect to the total weight of the composition.

The composition according to the invention can also comprise from 0.05 to 15% by weight, with respect to the total weight of emulsion, of at least one coemulsifier, which can be chosen from oxyethylenated sorbitan monostearate, fatty alcohols, such as stearyl alcohol or cetyl alcohol, or esters of fatty acids and of polyols, such as glycidyl stearate.

The composition according to the invention can also comprise one or more thickening agents in concentrations ranging up to 10% by weight, with respect to the total weight of the composition, chosen from:
polysaccharide biopolymers, such as xanthan gum, locust bean gum, guar gum, alginates, modified celluloses, starch derivatives, cellulose ether derivatives possessing quaternary ammonium groups, or cationic polysaccharides;
synthetic polymers, such as poly(acrylic acid)s, polyvinylpyrrolidone, poly(vinyl alcohol) or polymers based on polyacrylamide;
aluminium magnesium silicate.

Depending on the application envisaged, the composition can additionally comprise a film-forming polymer. This is in particular the case when it is desired to prepare a composition of nail varnish, mascara or eyeliner type or a hair composition of lacquer type. The polymers can be dissolved or dispersed in the cosmetically acceptable medium. In particular, the polymer can be present in the form of a solution in an organic solvent or in the form of an aqueous dispersion of particles of film-forming polymer. The said polymer can be chosen from nitrocellulose, cellulose acetobutyrate, poly(vinyl butyral)s, alkyd resins, polyesters, acrylics, vinyls and/or polyurethanes.

The composition can also comprise at least one plasticizer, which can be present at a content ranging from 1% to 40% by weight with respect to the total weight of the composition.

In addition, the composition can comprise a particulate phase, which can comprise pigments and/or pearlescent agents and/or fillers commonly used in cosmetic compositions.

The term "pigments" should be understood as meaning white or coloured, inorganic or organic particles intended to colour and/or opacify the composition.

The term "fillers" should be understood as meaning colourless or white, inorganic or synthetic, lamellar or non-lamellar particles intended to give body or stiffness to the composition and/or softness, mattness and uniformity to the make-up.

The term "pearlescent agents" is understood as meaning iridescent particles which reflect light.

The pigments can be present in the composition in a proportion of 0 to 50% by weight of the final composition and preferably in a proportion of 2 to 30% by weight. They can be white or coloured, inorganic and/or organic, and of conventional or nanometric size. Mention may be made of titanium, zirconium or cerium dioxides, as well as zinc, iron or chromium oxides, ferric blue, chromium hydrate, carbon black, ultramarines (aluminosilicate polysulphides), manganese pyrophosphate and some metal powders, such as silver or aluminium powders. Mention may also be made of lakes commonly employed to confer a make-up effect on the lips and skin, which lakes are calcium, barium, aluminium or zirconium salts, or acid colorants.

The pearlescent agents can be present in the composition in a proportion of 0 to 50% by weight, preferably at a level of the order of 1 to 25% by weight. Mention may be made, among pearlescent agents which can be envisaged, of natural mother-of-pearl, mica covered with titanium oxide, with iron oxide or natural pigments, bismuth oxychloride and coloured titanium oxide-coated mica.

The fillers, which can be present in a proportion of 0 to 80% by weight, preferably 1 to 60%, in the composition, can be inorganic or synthetic, lamellar or non-lamellar. Mention may be made of talc, mica, silica, kaolin, nylon and polyethylene powders, Teflon, starch, boron nitride, polymer microspheres, such as Expancel (Nobel Industrie), polytrap (Dow Corning) and silicone resin microbeads (Tospearls from Toshiba, for example), precipitated calcium carbonate, magnesium carbonate or hydrated magnesium carbonate, or metal soaps derived from organic carboxylic acids having from 8 to 22 carbon atoms.

Depending on the type of formulation, the pulverulent phase can represent from 0.01 to 99.5% by weight of the composition.

In addition, the composition can comprise a colorant, in particular a natural organic colorant, such as cochineal carmine, and/or a synthetic colorant, such as halo-acid, azo or anthraquinone colorants. Mention may be made of inorganic colorants, such as copper sulphate.

In addition, the composition can comprise any additive normally used in the cosmetic field, such as antioxidants, fragrances, essential oils, preservatives, lipophilic or hydrophilic cosmetic active principles, such as moisturizers, vitamins, sphingolipids, self-tanning agents, such as DHA, or sunscreen agents, antifoaming agents, sequestering agents or emollients.

Of course, a person skilled in the art will take care to choose the optional additional compounds and/or their amount so that the advantageous properties of the composition according to the invention are not, or not substantially, detrimentally affected by the envisaged addition.

The cosmetic compositions according to the invention can be provided in the form of a care and/or make-up product for the skin, an antisun or self-tanning product, or a hair product. They find a particular application in the make-up field, in particular as lipsticks, foundations, face powders, eyeshadows, free or compact powders, eyeliners, mascaras or nail varnishes.

The invention is illustrated in more detail in the following examples.

EXAMPLE 1

Preparation of 4,4'-dimethyloxy-[2,2'-binaphthylidene]-1,1'-dione 10 g of 4-methoxy-1-naphthol are dissolved, at room temperature, in a mixture of 1 liter of dimethylacetamide, 250 ml of methanol and 150 ml of water.

31 g of (2 equivalents) of ferric chloride hexahydrate are added, with stirring.

The mixture is left stirring for 5 minutes and then the blue precipitate is filtered off on sintered glass.

The compound is washed and dried in the usual way.

5.2 g (yield: 52%) of the desired pigment are obtained in the form of a blue/purple amorphous powder.

Melting point: 274° C.

HPTLC ($CH_2Cl_2$): single-spot profile, $R_f$=0.7

HPLC: single-peak profile

Mass, NMR and UV spectra: in accordance with the expected structure.

Elemental analysis:

|  | C % | H % | O % |
|---|---|---|---|
| Theoretical | 76.73 | 4.66 | 18.20 |
| Experimental | 76.94 | 4.64 | 18.53 |

The stability of this compound is tested and the following results are obtained:

stability at 90° C. at least 16 hours stability at 45° C. at least 1 month stability at pH 4: at least 1 month stability at pH 10: at least 1 month stability with regard to light (Suntest): at lest 36 hours.

EXAMPLE 2

Preparation of 4,4'-diethyloxy-[2,2'-binaphthylidene]-1,1'-dione 20 g of 4-ethoxy-1-naphthol are dissolved, at room temperature, in 500 ml of chloroform.

19 g of silver oxide are added, with stirring, and the reaction mixture is left stirring for 1 hour.

The precipitate is filtered off on sintered glass and washed with refluxing dichloromethane until the solvent is no longer coloured, the organic phase is concentrated and crystals with a dark purple colour are obtained, which crystals are dried.

10 g (yield: 50%) of the desired pigment are obtained in the form of crystals.

Melting point: 244° C.

HPTLC ($CH_2Cl_2$): single-spot profile, $R_f$=0.8

NMR spectrum: in accordance with the expected structure.

Elemental analysis:

| | Elemental analysis: | | |
|---|---|---|---|
|  | C % | H % | O % |
| Theoretical | 77.40 | 5.41 | 17.18 |
| Experimental | 77.46 | 5.30 | 17.03 |

EXAMPLE 3

Preparation of 4,4'-diisopropyloxy-[2,2'-binaphthylidene]-1,1'-dione

The preparation is carried out in a similar way to Example 2, from 20 g of 4-isopropyl-1-naphthol and 20 g of silver oxide.

16.4 g of purple crystals are obtained (yield: 83%).
Melting point: 230° C.
HPTLC (dichloromethane 8/heptane 2): single-spot profile, $R_f$=0.5
NMR spectrum: in accordance with the expected structure.
Elemental analysis:

| Elemental analysis: | | | |
| --- | --- | --- | --- |
| | C % | H % | O % |
| Theoretical | 77.98 | 6.04 | 15.98 |
| Experimental | 78.41 | 6.10 | 15.58 |

EXAMPLE 4

Preparation of 4,4'-di(n-hexyloxy)-[2,2'-binaphthylidene]-1,1'-dione

The preparation is carried out in a similar way to Example 2, from 7 g of 4-(n-hexyl)-1-naphthol and 14 g of silver oxide.

6.0 g of purple crystals are obtained (yield: 86%).
Melting point: 146° C.
HPTLC (dichloromethane 4/heptane 6): single-spot profile, $R_f$=0.2
NMR spectrum: in accordance with the expected structure.

EXAMPLE 5

Coating With Talc 0.6 g of 4,4'-dimethyloxy-[2,2'-binaphthylidene]-1,1'-dione is dissolved under warm conditions in 100 ml of dimethylformamide.

This mixture is run slowly onto a vigorously stirred suspension of 20 g of talc in 200 ml of water.

The suspension is allowed to cool to room temperature, filtered on sintered glass, washed with water and dried.

A pigment with a light blue homogeneous colour is obtained, which pigment is supported at 3% by weight on the talc.

EXAMPLE 6

2.05 g of 4,4'-dimethyloxy-[2,2'-binaphthylidene]-1,1'-dione are dissolved under warm conditions in 410 ml of dimethylformamide.

This mixture is run slowly onto a vigorously stirred suspension of 20.5 g of talc in 820 ml of water.

The suspension is allowed to cool to room temperature, filtered on sintered glass, washed with water and dried.

A pigment with a blue homogeneous colour is obtained, which pigment is supported at 10% by weight on the talc.

EXAMPLE 7

4.1 g of 4,4'-dimethyloxy-[2,2'-binaphthylidene]-1,1'-dione are dissolved under warm conditions in 820 ml of dimethylformamide.

This mixture is run slowly onto a vigorously stirred suspension of 20.5 g of talc in 1640 ml of water.

The suspension is allowed to cool to room temperature, filtered on sintered glass, washed with water and dried.

A pigment with a dark blue homogeneous colour is obtained, which pigment is supported at 20% by weight on the talc.

EXAMPLE 8

| An eyeshadow is prepared comprising the following ingredients: | |
| --- | --- |
| - Triisocetyl citrate | 0.275 g |
| - 4,4'-Dimethyloxy-[2,2'-binaphthylidene]-1,1'-dione (compound of Example 1) | 5 g |
| - Titanium dioxide | 2 g |
| - Bismuth oxychloride | 20 g |
| - Mica | 5 g |
| - Talc | 48.3 g |
| - Zinc stearate | 4 g |
| - Crosslinked poly(methyl methacrylate) | 10 g |
| - Dimethicone | 3.4595 g |
| - Dimethicone trimethylsiloxy-silicate | 1.089 g |
| - Cetyl dimethicone | 0.6765 g |
| - Methyl para-hydroxybenzoate | 0.2 g |

An eyeshadow with an intense blue colour is obtained which has very high coverage and which has very good hold on the eyelids.

The colour remains homogeneous and does not fade over time.

In addition, the eyeshadow does not migrate, does not bleed and does not form streaks on the eyelids after four hours.

EXAMPLE 9

Comparative

| An eyeshadow is prepared from the following ingredients: | |
| --- | --- |
| - Triisocetyl citrate | 0.275 g |
| - Manganese violet | 14 g |
| - Iron oxides | 2 g |
| - Ultramarine blue and silica | 25 g |
| - Cochineal carmine | 3 g |
| - Titanium dioxide | 2 g |
| - Bismuth oxychloride | 20 g |
| - Mica | 5 g |
| - Talc | 9.3 g |
| - Zinc stearate | 4 g |
| - Crosslinked poly(methyl methacrylate) | 10 g |
| - Dimethicone | 3.4595 g |
| - Dimethicone trimethylsiloxy-silicate | 1.089 g |
| Cetyl dimethicone | 0.6765 g |
| - Methyl para-hydroxybenzoate | 0.2 g |

An eyeshadow is obtained with a blue colour very similar to that obtained with the eyeshadow of Example 8 according to the invention.

Nevertheless, this eyeshadow does not cover as well.

In addition, tests of hold over time carried out on six subjects show poorer hold with a loss in intensity for one subject, a non-uniform tint or a tint which fades for two subjects and a tint which disappears for one subject.

The presence of streaks on the eyelids is observed for two subjects.

The results of the tests of hold over time on six subjects after four hours are as follows:

| Hold | Eyeshadow of Example 8 (invention) | Eyeshadow of Example 9 (comparative) |
|---|---|---|
| Very good | 2 | — |
| Good | 3 | 3 but loss in intensity (1) |
| Moderate | 1 loss in intensity | 2 non-uniform (1) very faded (1) |
| Poor | — | 1 the colour has disappeared |
| Presence of streaks | | |
| -yes | 1 | 2 |
| -no | 5 | 4 |

EXAMPLE 10

Microbiological Tests

The pigment of Example 1, namely 4,4'-dimethyloxy-[2,2'-binaphthylidene]-1,1'-dione, was compared with manganese violet.

Aspergillus niger and Penicillium chrysogenum mould spores are filtered. They are suspended in a diluent. Filtration is carried out and the filter is deposited at the surface of the pigment in the form of a powder. The number of microorganisms at the surface of each pigment is subsequently counted and the macroscopic growth of the moulds after incubating at 30° C. and 95% relative humidity for 21 days is evaluated.

The results are as follows:

| Microorganisms | Inoculum (microorganisms/filter) | Ageing at 30° C. (21 days) | |
|---|---|---|---|
| | | Pigment according to the invention | Manganese violet |
| Aspergillus niger | 7.0 × 10³ | 3.4 × 10⁴ | 7.0 × 10⁵ |
| Penicillium chrysogenum | 1.0 × 10⁴ | 4.8 × 10³ | 1.0 × 10⁶ |

After 21 days at 30° C., no macroscopic symptom is seen on the pigment according to the invention, whereas the manganese violet is completely overrun by moulds, which are visible with the naked eye; the macroscopic growth is intense.

What is claimed is:

1. A method of at least one of lengthing the hold of a cosmetic composition, decreasing or eliminating the migration potential of a cosmetic composition, decreasing or eliminating the transferability of a cosmetic composition and decreasing or eliminating the streak forming capacity of a cosmetic composition, said method comprising mixing at least one indigoid compound of formula:

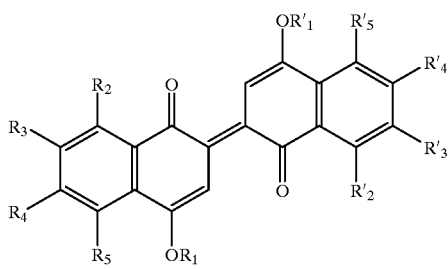

in which:
$R_1$ and $R'_1$ are, independently of one another, saturated or unsaturated, linear, branched or cyclic alkyl radicals having 1 to 18 carbon atoms which are optionally substituted by one or more halogens and/or by one or more hydroxyl radicals and/or interrupted by at least one heteroatom selected from the group consisting of oxygen, sulphur, nitrogen and silicon;

$R_2$, $R'_2$, $R_3$, $R'_3$, $R_4$, $R'_4$, $R_5$ and $R'_5$ are, independently of one another, chosen from a hydrogen atom, a halogen atom, a hydroxyl radical or a saturated or unsaturated, linear or branched, alkyl, alkyloxy, acyl or acyloxy radical having 1 to 6 carbon atoms, in a cosmetic composition.

2. A method of producing an antimicrobial cosmetic composition comprising mixing at least one indigoid compound of formula:

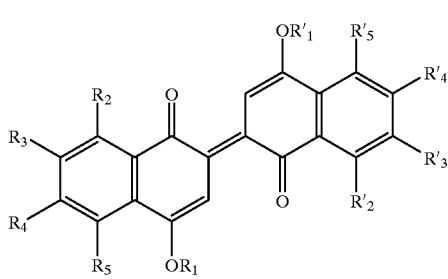

in which:
$R_1$ and $R'_1$ are, independently of one another, saturated or unsaturated, linear branched or cyclic alkyl radicals having 1 to 18 carbon atoms which are optionally substituted by one or more halogens and/or by one or more hydroxyl radicals and/or interrupted by at least one heteroatom selected from the group consisting of oxygen, sulphur, nitrogen and silicon;

$R_2$, $R'_2$, $R_3$, $R'_3$, $R_4$, $R'_4$, $R_5$ and $R'_5$ are, independently of one another, chosen from hydrogen atom, a halogen atom, a hydroxyl radical or a saturated or unsaturated, linear or branched, alkyl alkyloxy, acyl or acyloxy radical having 1 to 6 carbon atoms, in a cosmetic composition.

3. The method according to claim 1, wherein at least one of $R_1$ is an alkyl radical having 1 to 8 carbon atoms.

4. The method according to claim 1, wherein $R_2$ to $R_5$ and $R'_2$ to $R'_5$ are hydrogen.

5. The method according to claim 1 wherein the compound of formula (I) is present in a proportion of 0.5 to 30% by weight with respect to the total weight of the composition.

6. The method of claim 1 wherein the compound of formula (I) is present in the free form or in the form of a combination with substrate particles, which it coats.

7. The method of claim 6, wherein the substrate particles are selected from the group consisting of metal oxide pigments, metal oxide nanopigments, fillers, and microspheres.

8. Cosmetic composition comprising, in a cosmetically acceptable medium, at least one non-volatile silicone oil and at least one indigoid compound of formula:

(I)

in which:
- $R_1$ and $R'_1$ are, independently of one another, saturated or unsaturated, linear, branched or cyclic alkyl radicals having 1 to 18 carbon atoms which are optionally substituted by one or more halogens and/or by one or more hydroxyl radicals and/or interrupted by at least one heteroatom selected from the group consisting of oxygen, sulphur, nitrogen and silicon;
- $R_2$, $R'_2$, $R_3$, $R'_3$, $R_4$, $R'_4$, $R_5$ and $R'_5$ are, independently of one another, chosen from a hydrogen atom, a halogen atom, a hydroxyl radical or a saturated or unsaturated, linear or branched, alkyl, alkyloxy, acyl or acyloxy radical having 1 to 6 carbon atoms.

9. Cosmetic composition according to claim 8, wherein at least one $R_1$ and $R'_1$ is an alkyl radical having 1 to 8 carbon atoms.

10. Cosmetic composition according to claim 8 wherein $R_2$ to $R_5$ and $R'_2$ to $R'_5$ are hydrogen.

11. Cosmetic composition according to claim 8 wherein the compound of formula (I) is present in an amount of 0.5 to 30% by weight with respect to the total weight of the composition.

12. Cosmetic composition according to claim 8, wherein the compound of formula (I) is present in the free form or in the form of a combination with substrate particles, which it coats.

13. Cosmetic composition according to claim 12, wherein the substrate particles are selected from the group consisting of metal oxide pigments, metal oxide nanopigments, fillers, and microspheres.

14. Cosmetic composition according to claim 8, further comprising at least 0.5% by weight with respect to the total weight of the composition, of at least one silicone oil.

15. Cosmetic composition according to claim 14, wherein the silicone oil is at least one non-volatile silicone oil selected from the group consisting of polyalkylsiloxanes with a $C_1$–$C_{24}$ alkyl chain and with trimethylsilyl end groups alkyl, alkoxy or aryl dimethicone copolyols with a $C_1$–$C_{24}$ alkyl, alkoxy or aryl chain, silicones modified by optionally fluorinated aliphatic and/or aromatic groups or by hydroxyl, thiol and/or amine groups, and phenylated silicone oils.

16. Cosmetic composition according to claim 15, wherein the silicone oil is at least one of a dimethicone and an alkyl dimethicone.

17. Cosmetic composition according claim 14 comprising a volatile silicone oil.

18. Cosmetic composition according to claim 8 further comprising a non-silicone fatty substance selected from the group consisting of pasty fatty substances, gums, waxes and oils of vegetable, mineral, animal or synthetic origin.

19. Cosmetic composition according to claim 8, further comprising at least one of a pigment, a nanopigment, a pearlescent agent and a filler.

20. Cosmetic composition according to claim 8, further comprising at least one additive selected from the group consisting of antioxidants, fragrances, essential oils, preservatives, cosmetic or dermatological active principles, anti-foaming agents, sequestering agents, emollients, fat-soluble polymers and dispersions of film forming polymer particles in an aqueous medium.

21. Cosmetic composition according to claim 8, provided in the form of a suspension, of a dispersion or of a solution in solvent or aqueous/alcoholic medium which is optionally thickened or gelled, of an oil-in-water, water-in-oil or multiple emulsion, of a gel or of a foam, of an emulsified gel, of a dispersion of vesicles, of a two-phase or multiphase lotion, of a spray, of a free, compact or cast powder, or of an anhydrous paste.

22. Cosmetic composition according to claim 8, provided in the form of a make-up product for the skin, lips, nails, eyelashes, eyebrows or hair.

23. Cosmetic composition according to claim 8, provided in the form of an eyeshadow, of a face powder, of a foundation or of a free or compact powder for the face.

24. The method according to claim 1 wherein the compound of formula (I) is selected from the group consisting of:
- 4,4'-dimethyloxy-[2,2'-binaphthylidene]-1,1'-dione,
- 4,4'-diethyloxy-[2,2'-binaphthylidene]-1,1'-dione,
- 4,4'-diisopropyloxy-[2,2'-binaphthylidene]-1,1'-dione, and
- 4,4'-di (n-hexyloxy)-[2,2'-binaphthylidene]-1,1'-dione.

25. The method of claim 24, wherein the compound of formula (I) is 4,4'-dimethyloxy-[2,2'-binaphthylidene]-1,1'-dione.

26. The method of claim 9, wherein the substrate particles are selected from the group consisting of talc, mica, silica, kaolin, or nylon and polyethylene powders, and hollow microspheres formed of vinylidene chloride/acrylonitrile copolymers.

27. Cosmetic composition according to claim 8, wherein the compound of formula (I) is selected from the group consisting of
- 4,4'-dimethyloxy-[2,2'-binaphthylidene]-1,1'-dione,
- 4,4'-diethyloxy-[2,2'-binaphthylidene]-1,1'-dione,
- 4,4'-diisopropyloxy-[2,2'-binaphthylidene]-1,1'-dione, and
- 4,4'-di (n-hexyloxy)-[2,2'-binaphthylidene]-1,1'-dione.

28. Cosmetic composition according to claim 27, wherein the compound of formula (I) is 4,4'-dimethyloxy-[2,2'-binaphthylidene]-1,1'-dione.

29. Cosmetic composition according to claim 13, wherein the substrate particles are selected from the group consisting of talc, mica, silica, kaolin, or nylon and polyethylene powders, and hollow microspheres formed of vinylidene chloride/acrylonitrile copolymers.

30. The method according to claim 2 wherein at least one $R_1$ and $R'_1$ is an alkyl radical having 1 to 8 carbon atoms.

31. The method according to claim 2, wherein $R_2$ to $R_5$ and $R'_2$ to $R'_5$ are hydrogen.

32. The method according to claim 2 wherein the compound of formula (I) is present in a proportion of 0.5 to 30% by weight, with respect to the total weight of the composition.

33. The method of claim 2 wherein the compound of formula (I) is present in the free form or in the form of a combination with substrate particles, which it coats.

34. The method of claim 33, wherein the substrate particles are selected from the group consisting of metal oxide pigments, metal oxide nanopigments, fillers, and microspheres.

35. The method according to claim 2 wherein the compound of formula (I) is selected from the group consisting of:

4,4'-dimethyloxy-[2,2'-binaphthylidene]-1,1'-dione, 4,4'-diethyloxy-[2,2'-binaphthylidene]-1,1'-dione, 4,4'-diisopropyloxy-[2,2'-binaphthylidene]-1,1'-dione, and 4,4'-di (n-hexyloxy)-[2,2'-binaphthylidene]-1,1'-dione.

36. The method of claim 35, wherein the compound of formula (I) is 4,4'-dimethyloxy-[2,2'-binaphthylidene]-1,1'-dione.

37. The method of claim 34, wherein the substrate particles are selected from the group consisting of talc, mica, silica, kaolin, or nylon and polyethylene powders, and hollow microspheres formed of vinylidene chloride/acrylonitrile copolymers.

* * * * *